United States Patent [19]

Mueller

[11] 4,297,487
[45] Oct. 27, 1981

[54] PHOSPHONIUM SALTS

[75] Inventor: Richard A. Mueller, Glencoe, Ill.

[73] Assignee: G. D. Searle & Co., Skokie, Ill.

[21] Appl. No.: 175,791

[22] Filed: Aug. 6, 1980

[51] Int. Cl.³ .............................................. C07F 9/54
[52] U.S. Cl. ................... 542/412; 260/333;
260/345.1; 260/345.2; 260/345.9 R;
260/346.11; 260/346.22; 260/347.8; 424/203
[58] Field of Search ................. 260/333, 345.1, 345.2,
260/345.9 R, 346.11, 346.22, 347.8; 424/203;
542/412

[56] References Cited

U.S. PATENT DOCUMENTS 4,075,407 2/1978 Mueller .............................. 542/412

Primary Examiner—Richard Raymond
Attorney, Agent, or Firm—Albert Tockman; W. Dennis Drehkoff

[57] ABSTRACT

Phosphonium salts represented by the formula

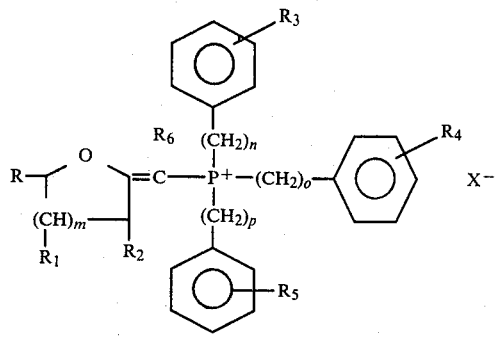

wherein: R is selected from the group consisting of lower alkyl, phenyl, substituted phenyl, benzyl and substituted benzyl; $R_1$ is hydrogen or lower alkyl; $R_2$ is hydrogen or loweralkyl; or $R_1$ and $R_2$ taken together form a 5 or 6 membered saturated or unsaturated carbocyclic ring with the limitation that $R_1$ is on the carbon atom adjacent the carbon atom bearing $R_2$, m is 1,2 or 3; n is 0 or 1; o is 0 or 1; p is 0 or 1; $R_3$, $R_4$ and $R_5$ are the same or different members of the group consisting of hydrogen, lower alkyl, lower alkoxy and halo; $R_6$ is hydrogen or $C_1$—$C_3$ straight or branched chain alkyl; and X is a pharmaceutically acceptable anion. Compounds wherein R is phenyl, substituted phenyl, benzyl or substituted benzyl are narcotic antagonists. Compounds wherein $R_1$ and $R_2$ are hydrogen or lower alkyl when R is lower alkyl are mixed agonist/antagonist analgesic agents and compounds where $R_1$ and $R_2$ taken together form a carbocyclic ring are analgesic agents.

16 Claims, No Drawings

PHOSPHONIUM SALTS

BACKGROUND OF THE INVENTION

While there are a number of commercially available mild to moderate analgesic agents, the search for alternative analgesic agents has continued because of the problems attendant with current therapy.

Aspirin and related salicylates are considered to be non-narcotic analgesic agents useful for relieving mild to moderate pain, in addition to their anti-inflammatory and anti-pyretic properties. However, the ingestion of salicyclic acid or related salycilates may result in epigastric distress, nausea and vomiting. This widely used class of non-narcotic analgesic agents may also cause gastric ulceration and even hemorrhage both in experimental animals and man. Exacerbation of peptic ulcer symptoms and erosive gastritis have all been reported in patients on high dose therapy, i.e., arthritis patients. Aspirin is also one of the most common causes of drug poisoning in young children and has a potential of serious toxicity if used improperly.

Acetominophen is also considered to be a non-narcotic analgesic agent useful in treating pain associated with simple headache, common muscular aches, etc. While acetominophin is particularly useful for patients who cannot take aspirin, i.e. ulcer patients, its use in contraindicated in individuals who have exhibited a sensitivity to it.

In addition to their drawbacks in view of their potential side effects, the mild, non-narcotic analgesic agents are not sufficiently potent to relieve the severe pain associated with surgery, cancer and the like.

Unfortunately, the potent analgesic agents capable of relieving such severe pain are also narcotic agents and their use entails the risk of producing physical or psychological dependence.

One moderate analgesic agent which has enjoyed great commercial success for a number of years α-d-propoxyphene hydrochloride (Darvon ®, Eli Lilly and Co., Indianapolis, Ind.) has been widely used to relieve pain associated with dental extractions, afterbirth pain, and some post-operative pain. This widely used analgesic agent has been reported to be ineffective in relieving many types of pain, and recently, reports of serious side effects and deaths have created a need for alternative, moderate analgesic agents. The present invention provides such agents.

There also is a continuing need for alternative narcotic antagonists because of the side effects of the presently available agents. The present invention also provides such agents.

SUMMARY OF THE INVENTION

The present invention provides novel phosphonium salts which are useful as analgesic agents and narcotic antagonist agents. The compounds are represented by the formula;

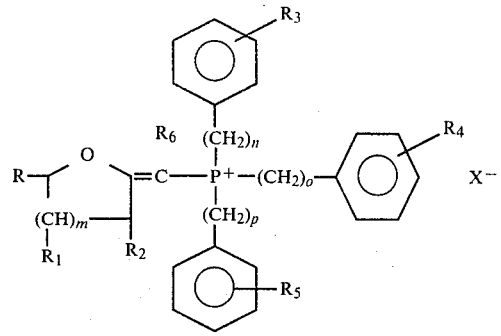

wherein: R is selected from the group consisting of lower alkyl, phenyl, substituted phenyl, benzyl and substituted benzyl; $R_1$ is hydrogen or lower alkyl; $R_2$ is hydrogen or loweralkyl; or $R_1$ and $R_2$ taken together form a 5 or 6 membered saturated or unsaturated carbocyclic ring with the limitation that $R_1$ is on the carbon atom adjacent the carbon atom bearing $R_2$, m is 1,2 or 3; n is 0 or 1; o is 0 or 1; p is 0 or 1; $R_3$, $R_4$ and $R_5$ are the same or different members of the group consisting of hydrogen, lower alkyl, lower alkoxy and halo; $R_6$ is hydrogen or $C_1$–$C_3$ straight or branched chain alkyl; and X is a pharmaceutically acceptable anion. Compounds wherein R is phenyl, substituted phenyl, benzyl or substituted benzyl are narcotic antagonists. Compounds wherein $R_1$ and $R_2$ are hydrogen or lower alkyl when R is lower alkyl are mixed agonist/antagonist analgesic agents and compounds where $R_1$ and $R_2$ taken together form a carbocyclic ring are analgesic agents.

In the case of the analgesic agents of the present invention, the compounds are administered to mammalian patients suffering from mild to moderate pain in parenteral dosages of from 3 to 35 mg/kg of body weight daily, preferably in divided dosages, until the pain has subsided. Generally, the compounds are administered every four to six hours unless they are formulated as sustained release formulations, in which case they are administered every 8 to 12 hours.

In the case of the narcotic antagonists of the present invention, the compounds are administered to patients on an acute basis in the case of a drug overdose, or on a chronic basis to effect withdrawal of narcotic addiction. The compounds can be administered parenterally in acute dosages of from 15 to 35 mg/kg and in chronic dosages of from 3 to 35 mg/kg daily.

DETAILED DESCRIPTION OF PREFERRED EMBODIMENTS

As used herein, the term "lower alkyl" refers to straight and branched chain alkyl groups having from one to six carbon atoms such as methyl, ethyl, n-propyl, iso-propyl, n-butyl, iso-butyl, tert-butyl, n-pentyl, 2-methylbutyl, 2,2-dimethylpropyl, n-hexyl, etc.

The term "substituted phenyl" refers to a mono-, di-, or tri-substituted phenyl radical, substituted with the same or different members of the group consisting of lower alkyl, lower alkoxy, halo, nitro, cyano, halo lower alkyl, hydroxy, alylcarbonyl, etc.

The term "substituted benzyl" refers to a mono-, di-, or tri-substituted benzyl groups, substituted with the same or different members of the group consisting of lower alkyl, lower alkoxy, halo, nitro, cyano, halo lower alkyl, hydroxy, etc.

The term "lower alkoxy" refers to straight or branched chain $C_1-C_6$ alkoxy groups, i.e., methoxy, ethoxy, isopropoxy, etc.

The term "anions" includes, but is not limited to pharmaceutically acceptable (non-toxic) anions such as chloride, bromide, iodide, fluoride, acetate, propionate, sulfate, bisulfate, acetate, oxalate, valerate, oleate, laurate, borate, citrate, maleate, fumarate, lactate, succinate, tartrate, benzoate, tetrafluoroborate, trifluoromethyl sulfonate, napsylate, tosylate, etc.

The analgesic activity of the compounds of the present invention was initially established in the mouse writhing test.

The narcotic antagonist activity was originally established in a modification of the mouse hot plate test, conducted as follows: Groups of 10 mice are place individually under an inverted restraining cylinder on a hot plate with the temperature controlled at 55° C.±0.3° C. The reaction time of of each mouse to lick a foot or jump is measured. Any mouse not responding within 15 seconds is discarded. Fifteen minutes following this pretrial, each mouse is given an injection of a mixture of saline and 3–5 drops of propylene glycol and Tween 80 ® wetting solution (50/50, vehicle) or test compound dissolved in the vehicle. Fifteen minutes following this administration, each mouse is injected subcutaneously with 40 mg/kg of morphine sulfate, a dose previously found to produce "maximum analgesia" for approximately 2 hours in the hot plate test. Injections are given in a volume of 0.1 mg/10 kg of body weight. Fifteen, 30, 60 and 90 minutes following morphine administration, the reaction time of each mouse to lick a foot or jump is measured. Any mouse not responding within 30 seconds is terminated for that trial. By means of the Wilcoxon rank sum test, comparisons of the mean reaction times are made between the vehicle treated group (controls) and the test compound treated group at each of the post-treatment intervals. A compound is rated active as a narcotic antagonist if the analgesic response is significantly different as compared to the controls at 3 or more of the post treatment invervals (Wilcoxon rank sum test, $p<0.05$, 1 tail).

The preparation of the compounds of the present invention is illustrated in the examples set forth hereinbelow. Generally speaking, the compounds of the present invention are prepared by cyclization of a hydroxyphosphorane. The synthesis of the hydroxyphosphorane intermediates, as well as the method of cyclization is illustrated in the following examples and set forth in my commonly assigned, copending patent application U.S. Ser. No. 06/172,781., filed July, 1980.

Synthesis of the halophosphorane intermediates from a halocarboxylic acid as well as methods of cyclization of these intermediates is disclosed in my commonly assigned U.S. Pat. No. 4,075,407.

Hydroxyphosphorane cyclization is an acid catalyzed cyclization/elimination sequence, whereas the halophosphorane procedure involves a nucleophilic substitution. Therefore, the choice of the most convenient method is best determined by one skilled in the art, based on steric, electronic, and cost factors as well as ease of purification, storage, etc. of the intermediates The following examples further illustrate the present invention.

EXAMPLE 1

Preparation of [2-oxo-(2-hydroxymethylphenyl)ethyl]triphenylphosphorane

Methyltriphenyl phosphonium bromide (22 g, Aldrich Chemical Co., Milwaukee, Wis.) was suspended in tetrahydrofuran (200 ml) with stirring under an argon atmosphere. The suspension was cooled to approximately −78° C. in a dry ice-acetone bath, and phenyl lithium (35 ml, 1.87 M) was added dropwise over a period of about 1 hour. When the addition was complete, the solution was allowed to warm to room temperature overnight. Dimethylsulfoxide was added until all solids had dissolved and the reaction mixture was clear. The solution was stirred at room temperature, cooled to approximately 10° C. and phthalide (4.22 g) added thereto in one portion and stirred at room temperature for 5 hours. The latter reaction mixture was poured into water (1 liter), stirred vigorously for one half hour and extracted four times with benzene. The benzene extracts were combined, washed 3 times with 250 ml portions of water, twice with 250 ml portions of saturated sodium chloride solution, and dried over sodium sulfate. Partial removal of solvent gave 17.2 g of product. Chromatography on silica packed and eluted with 30% ethyl acetate in methylene chloride gave 5.4 g of product having the formula:

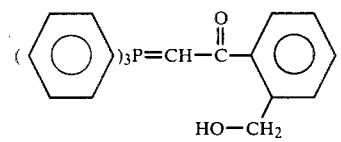

EXAMPLE 2

Preparation of [(1,3-dihydroisobenzofuran-1-ylidine)]triphenylphosphonium chloride

[2-Oxo-(2-hydroxymethylphenyl)ethyl]triphenylphosphorane (1.6 g) was dissolved in 60 ml of methanol and 3.6 ml of concentrated hydrochloric acid was added thereto and the solution refluxed gently for about 3 days. The solvents were removed on a rotary evaporator at approximately 60° C. under a water aspirator vacuum to give crystalline product which can be recrystallized from methyl ethyl ketone to give product having the following elemental analysis and structure:

Analysis Calcd. for $C_{27}H_{22}ClOP$: C,75.51; H,5.33; P,7.18. Found: C,75.60; H,5.17; P,7.22.

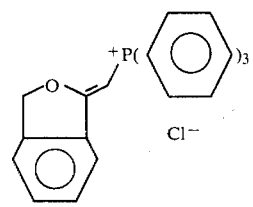

EXAMPLE 3

Preparation of (5-hydroxy-2-oxo-5-phenylpentyl)triphenylphosphorane

Following the method of Example 1, methyltriphenylphosphonium bromide (22 g), tetrahydrofuran (200 ml), phenyl lithium (35 ml) dimethylsulfoxide and 4-phenyl-γ-butyrolactone (5 g) were reacted to yield 8 g of crude product. Column chromatography on 250 g of silica, packed and eluted with ethyl acetate-benzene [5:50(v/v)] resulted in pure product: PMR(CDCl$_3$) δ2.05(2H,m),2.6(2H,m),3.8(1H,d,J=27 Hz),4.8(1H,t,J=6.5 Hz 7.5(20H,m) and having the formula

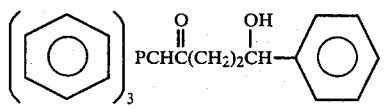

EXAMPLE 4

Preparation of triphenyl[tetrahydro-5-phenyl-furan-2-ylidene)methyl]phosphonium tetrafluoroborate 1.5 Grams of the product of Example 3 was dissolved in 20 ml of methylene chloride and 5.5 ml of approximately 1.0 M triethyloxonium tetrafluoroborate in methylene chloride was added. The solution was stirred at room temperature for about 45 minutes and then 20 ml of water was added and stirring continued for 15 minutes. The layers were separated and the aqueous phase extracted again with 20 ml of methylene chloride. The extracts were combined, dried over sodium sulfate and the solvent removed to give an oil which crystallized upon trituration with acetone. Recrystallization from methyl ethyl ketone and warming for 5 hours at 85° C. and 0.3 mm pressure gave the desired product, m.p. 185°–187° C. and having the formula:

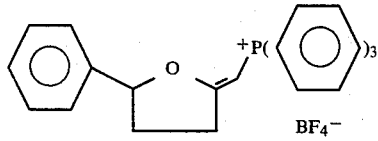

EXAMPLE 5

Preparation of (5-hydroxy-2-oxyhexyl)triphenylphosphorane

Following the method of Example 1, methyltriphenylphosphonium bromide (22 g), tetrahydrofuran (200 ml) phenyl lithium (35 ml, 1.87 M), dimethylsulfoxide and 4-methylbutyrolactone (5.8 ml) were reacted to yield 15 g of crude product. Column chromatography of the latter on silica, packed and eluted with four percent ethanol-methylene chloride, yielded 6.8 g of (5-hydroxy-2-oxohexyl)triphenylphosphorane: PMR(CDCl$_3$) δ 1.18(3H,d,J=6 Hz),1.8(2H,m),2.55(2H,m),3.85(2H,m),7.5(15H,m); and having the formula

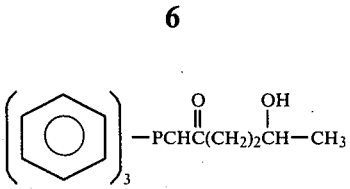

EXAMPLE 6

Preparation of triphenyl[(tetrahydro-5-methyl-furan-2-ylidene)methyl]phosphonium tetrafluoroborate 1.5 g of (5-hydroxy-2-oxohexyl)triphenylphosphorane was dissolved in 20 ml of methylene chloride under a nitrogen atmosphere, cooled in dry ice/acetone bath and 15 ml of triethyloxonium tetrafluoroborate as a 1 M solution in methylene chloride was added. The reaction mixture was stirred at about −78 C. for 0.5 hour and allowed to warm to room temperature over about 2 hours, decanted into ice water and stirred vigorously with the addition of an additional 30 ml of methylene chloride. The extraction was repeated twice, the extracts combined, and solvent removed to afford the desired product, m.p. 118.5°–122° C. and having the formula

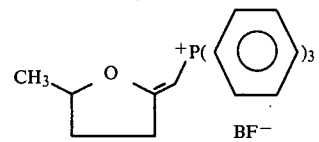

The above examples illustrate the preparation of the analgesic and antagonist agents of the present invention. In addition to the final products, deuterated compounds can be prepared for labelling and analyses purposes. The following examples illustrate deuteration.

EXAMPLE 7

Preparation of triphenyl[tetrahydro-2H-pyran-2-ylidene-3,3-d2)methyl-d]phosphonium chloride 200 Milligrams of 5-chloro-pentanoylmethylenetriphenylphosphonium chloride (U.S. Pat. No. 4,075,407) was dissolved in 6 ml of D$_2$O and stirred for about 18 hours under argon. Potassium carbonate (182 mg) was dissolved in 2 ml of D$_2$O and this solution was added to the phosphonium salt solution in one portion with stirring at room temperature for one hour. The heterogeneous mixture was then heated at reflux for one hour, allowed to cool to room temperature overnight, filtered, diluted to 25 ml with water and extracted 3 times with 20 ml portions of methylene chloride. The organic extracts were combined, dried over sodium sulfate, and the solvent removed under a nitrogen stream and the product dried at room temperature for 2 hours at 0.2 mm pressure to give 184 mg of crystals. Recrystallization from acetone gave the final product, m.p. 216°–218° C.

Analysis Calcd. for $C_{24}H_{21}D_3ClOP$: C,72.44; H,6.12; P,7.74. Found: C,72.77; H,6.14; P,7.78.

EXAMPLE 8

Preparation of [(2-oxepanylidene-3,3-d$_2$)methyl-d]triphenylphosphonium bromide The title compound was prepared by the method of Example 7 from 6-bromohexanoylmethylenetriphenylphosphonium bromide.

EXAMPLE 9

Preparation of [(tetrahydro-2-H-furan-2-ylidene-3,3-d$_2$)-methyl-d]triphenylphosphonium chloride The title compound was prepared by the method of Example 7 from 4-chlorobutyrylmethylenetriphenylphosphonium chloride.

The deuterated compounds of the present invention are represented by the formula:

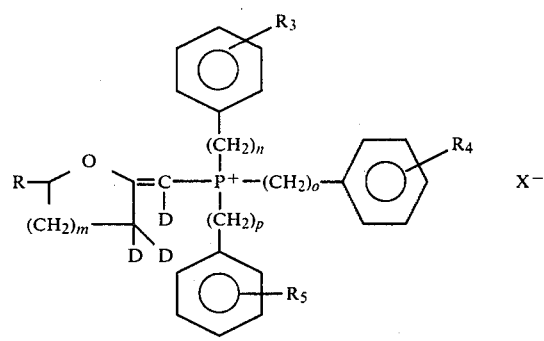

Pharmaceutical compositions comprising a therapeutically effective amount of a compound of the present invention and a pharmaceutically acceptable carrier or diluent are also provided by the present invention.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides, inert diluents, such compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

I claim:

1. A phosphonium salt represented by the formula:

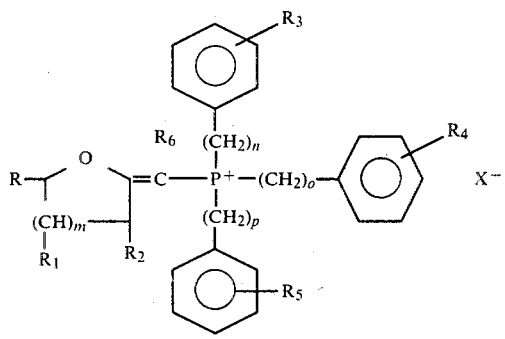

wherein: R is selected from the group consisting of phenyl, substituted phenyl, benzyl and substituted benzyl; R$_1$ is hydrogen or lower alkyl; R$_2$ is hydrogen or loweralkyl; or R$_1$ and R$_2$ taken together form a 5 or 6 membered saturated or unsaturated carbocyclic ring with the limitation that R$_1$ is on the carbon atom adjacent the carbon atom bearing R$_2$, m is 1,2 or 3; n is 0 or 1; o is 0 or 1; p is 0 or 1; R$_3$, R$_4$ and R$_5$ are the same or different members of the group consisting of hydrogen, lower alkyl, lower alkoxy and halo; R$_6$ is hydrogen or C$_1$-C$_3$ straight or branched chain alkyl; and X is a pharmaceutically acceptable anion.

2. A compound of claim 1 wherein m is 1.
3. A compound of claim 1 or 2 wherein R$_1$ is hydrogen.
4. A compound of claim 3 wherein n,o and p each are 0.
5. A compound of claim 2, 3 or 4 wherein R$_6$ is hydrogen.
6. A compound of claim 2: a pharmaceutically acceptable salt of triphenyl[tetrahydro-5-phenyl-furan-2-ylidene)methyl]phosphonium.
7. A compound of claim 1 wherein m is 2.
8. A compound of claim 7 wherein n,o and p each are 0.
9. A compound of claim 7 wherein n,o and p each are 1.
10. A compound of claim 2 wherein n,o and p each are 1.
11. A compound of claim 7, 8 or 9 wherein R$_6$ is hydrogen.
12. A compound of claim 1 wherein m is 3.
13. A compound of claim 12 wherein n,o and p each each are 0.
14. A compound of claim 12 wherein n,o and p each are 1.
15. A compound of claim 1 wherein R$_1$ and R$_2$ taken together form a 5 or 6 membered saturated or unsaturated carbocyclic ring.
16. A compound of claim 15: a [(1,3-dihydroisobenzofuran-1-ylidene)triphenyl]phosphonium salt.

* * * * *